(12) United States Patent
Hörlle et al.

(10) Patent No.: US 9,724,152 B2
(45) Date of Patent: Aug. 8, 2017

(54) ELECTRODE ARRANGEMENT AND ELECTROSURGICAL GRIPPING INSTRUMENT

(75) Inventors: Andreas Hörlle, Berlin (DE); Hanno Winter, Berlin (DE); Adrian Schulze, Berlin (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 581 days.

(21) Appl. No.: 14/342,429

(22) PCT Filed: Aug. 31, 2012

(86) PCT No.: PCT/EP2012/066977
§ 371 (c)(1),
(2), (4) Date: Apr. 21, 2014

(87) PCT Pub. No.: WO2013/030349
PCT Pub. Date: Mar. 7, 2013

(65) Prior Publication Data
US 2014/0228844 A1    Aug. 14, 2014

(30) Foreign Application Priority Data
Sep. 2, 2011 (DE) .................. 10 2011 082 102

(51) Int. Cl.
*A61B 18/08* (2006.01)
*A61B 18/14* (2006.01)
*A61B 18/00* (2006.01)

(52) U.S. Cl.
CPC .......... *A61B 18/082* (2013.01); *A61B 18/085* (2013.01); *A61B 18/1442* (2013.01);
(Continued)

(58) Field of Classification Search
CPC .... A61B 2018/00172; A61B 2018/178; A61B 2560/04; A61B 2560/0406;
(Continued)

(56) References Cited

U.S. PATENT DOCUMENTS

2003/0125732 A1* 7/2003 Goble .................. A61B 18/14
606/48
2003/0125734 A1    7/2003 Mollenauer
(Continued)

FOREIGN PATENT DOCUMENTS

DE    20 2004 010 311 U1    9/2004
DE    11 2008 000 288 T5    1/2010
(Continued)

OTHER PUBLICATIONS

Feb. 8, 2016 Office Action issued in Japanese Patent Application No. 2014-527676.
(Continued)

*Primary Examiner* — Joseph Stoklosa
*Assistant Examiner* — Nicole L Pobre
(74) *Attorney, Agent, or Firm* — Oliff PLC

(57) ABSTRACT

The invention relates to an electrode arrangement for an electrosurgical gripping instrument with an electrode, a heating element and a resilient insulator arranged between the electrode and the heating element to insulate them from one another, wherein the insulator is soft relative to bending. The invention further relates to an electrosurgical gripping instrument with an electrode arrangement according to the invention.

13 Claims, 5 Drawing Sheets

(52) U.S. Cl.
CPC ......... *A61B 2018/0063* (2013.01); *A61B 2018/00083* (2013.01); *A61B 2018/00095* (2013.01); *A61B 2018/00797* (2013.01); *A61B 2018/00994* (2013.01)

(58) Field of Classification Search
CPC ............ A61B 2562/16; A61B 2562/22; A61B 2562/225; A61B 2562/227
See application file for complete search history.

(56) References Cited

U.S. PATENT DOCUMENTS

| | | | |
|---|---|---|---|
| 2003/0129382 A1* | 7/2003 | Treat | A61B 18/085 428/316.6 |
| 2005/0016992 A1 | 1/2005 | Aoki | |
| 2006/0155273 A1* | 7/2006 | Swanson | A61B 18/1442 606/51 |
| 2008/0015575 A1 | 1/2008 | Odom et al. | |
| 2008/0187989 A1 | 8/2008 | McGreevy et al. | |
| 2009/0248002 A1 | 10/2009 | Takashino et al. | |
| 2013/0253508 A1 | 9/2013 | Ide | |

FOREIGN PATENT DOCUMENTS

| | | |
|---|---|---|
| EP | 1 878 399 A1 | 1/2008 |
| EP | 2 106 762 A1 | 10/2009 |
| EP | 2 111 812 A1 | 10/2009 |
| JP | 2005-040408 A | 2/2005 |
| JP | 2009-247893 A | 10/2009 |
| JP | 2012-125339 A | 7/2012 |

OTHER PUBLICATIONS

International Search Report issued in International Application No. PCT/EP2012/066977 mailed Nov. 27, 2012.

Written Opinion of the International Searching Authority issued in International Application No. PCT/EP2012/066977 mailed Nov. 27, 2012.

Nov. 4, 2015 Office Action issued in Chinese Patent Application No. 201280042185.1.

Translation of Jun. 20, 2016 Office Action issued in Japanese Patent Application No. 2014-527676.

* cited by examiner

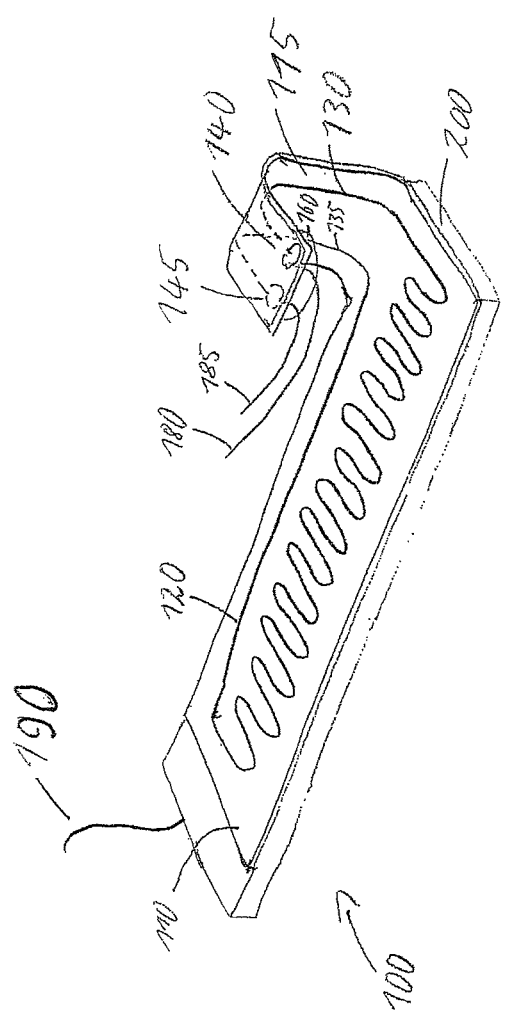

ELECTRODE ARRANGEMENT AND ELECTROSURGICAL GRIPPING INSTRUMENT

The invention relates to an electrode arrangement for an electrosurgical gripping instrument including an electrode, a heating element and an insulator arranged between the electrode and the heating element insulating them from one another. The invention furthermore relates to an electrosurgical gripping instrument with a jaw.

Electrosurgical gripping instruments are used to coagulate and/or transect tissue, for example blood vessels. Further, they are used to fuse two loose tissue sections, i.e. to permanently seal them, thereby rendering a suture redundant. For this purpose, electrosurgical gripping instruments typically have two jaws between which the tissue to be coagulated, transected or fused is gripped. Typically, electrode arrangements are arranged on the jaws, through which a high frequency (HF) voltage can be applied to the tissue.

In particular applications, like e.g. during fusion, it can be advantageous to have, in addition to the electrode, also a heating element in the instrument. Thus, e.g. fusion can initially be performed through HF energy and, subsequently, when the increased tissue resistance stops the fusion through HF, the fusion can be continued through the thermal energy of the heating element. The electrodes are heated in order to provide a current-independent application of energy. For this purpose, heating elements can be provided for heating the electrode. Since current flows through the electrode as well as through the heating elements, they have to be insulated from one another. Typically, this is implemented through a ceramic insulator. However, there is the risk with ceramic insulators that they crack under the high pressure which occurs during coagulation and transection and thus lose their insulating property.

Document DE 202004 010 311 U1 illustrates a heating element at branches.

Document DE 11 2008 000 288 T5 illustrates a device for tissue fusion, which also operates only thermally.

Document US 2008/0 015 575 A1 also illustrates a device for tissue fusion through heat.

A heating element is furthermore described in EP 2 106 762 A1.

It is desirable also to increase the reliability of the electrode arrangement.

According to the invention, this is facilitated by an electrode arrangement and by an electrosurgical gripping instruments according to the independent claims. Advantageous embodiments can be derived from the respective dependent claims.

According to a first aspect, the invention relates to an electrode arrangement for an electrosurgical gripping instrument. The arrangement includes an electrode, a heating element and an insulator arranged between the electrode and the heating element insulating both elements from one another. The insulator is resilient.

The inventors have found that the reliability of the electrode arrangement can be affected due to the fact that, during exertion of high pressure on a tissue, a jaw of a gripping instrument on which the electrode arrangement is arranged may bend. Thereby, a high tensile stress is exerted on the insulator. The electrode arrangement according to the first aspect of the invention facilitates that the insulator does not break upon bending.

An insulator according to this application is basically an electrical insulator, i.e. a material with a sufficiently high electrical resistance for preventing a current flow. Preferably, the insulator has a good thermal conductivity.

An electrode typically consists of a conductive material, and in particular of a biocompatible material. In this respect, e.g. various metals are suitable. Preferably, the electrode is flat which facilitates to achieve a planar, even contact surface towards the tissue.

Typically the electrode is inflexible, in particular substantially more inflexible than the insulator. The electrode thus provides a flat contact surface which however can bend to a greater or lesser extent under forces being exerted during the application. Alternatively, the electrode can also be easily ductile, e.g. resilient. In this case, it can adapt itself to uneven tissue.

The electrode can be configured as a layer on the side of the insulator facing away from the heating element. This can be facilitated e.g. through a coating method in which the insulator is coated with the electrode. In this case, the electrode would be a coating of the insulator.

However, the reverse arrangement is also advantageous. Thereby, the insulator is coated onto the electrode. The coating prevents air blowing between electrode and insulator. Here, the electrode forms the supporting element of the electrode arrangement.

The heating element typically consists of a material which has a suitable resistance so that a current flowing through causes heating. The generated heat is transferred to the electrode through the insulator. The electrode transfers the heat to the tissue. The heating element can e.g. consist fully or partially of an iron-nickel-alloy.

The heating element has preferably a flat configuration. It can e.g. be configured as a layer on the insulator. Particularly preferably, the heating element covers a major portion of a surface of the insulator, for example more than 80% of a surface of the insulator. The insulator, in turn, preferably covers at least 90% of the surface of the electrode. Thereby, a particularly even generation and distribution of heat is achieved.

It should be pointed out that the resilient configuration of the insulator according to the invention ensures the reliability of the insulator also when a flat heating element is used. The insulator can also consist of thin layers of ceramic, glass or silicon, which thus are flexible, too. Preferably, the material thickness is then a few tenths of a millimeter. Preferably, the heating element is configured at least 2 times as thick, particularly preferably at least 4 times as thick as the insulator.

The electrode arrangement preferably has one or multiple recesses for temperature sensors. With such temperature sensors, the temperature of the electrode or of treated body tissue can be monitored. These can be optical temperature sensors. The recesses can be configured for example in the form of holes in a flat heating element.

As an alternative to a flat heating element, the heating element, however, can also be configured as a heating wire which is arranged on the insulator in a suitable manner. For example, the heating wire can be installed at least partially folded or in helical form. Thereby, even heat generation can also be achieved.

Preferably, the insulator consists wholly or partially made of flexible plastic material. Polyimide is particularly suitable for this purpose. A suitable plastic material is made for example through polycondensation of an aromatic dianhydride and an aromatic diamine. A particularly suitable plastic material is for example poly (4,4'-oxdiphenylen-pyromelitimide), which is also sold under the trade name Kapton by DuPont Inc.

Preferably, the insulator has a flat structure. According to a preferred embodiment, the insulator is a foil made from insulating, resilient plastic material onto which the heating element and feed lines to the heating element are applied. Using a foil facilitates an embodiment that can be produced in a particularly simple manner. The heating element can be processed together with the foil after its application onto the foil.

Preferably, the heating element, the insulator and the electrode form a layered stack. This yields a particularly simple and robust embodiment of the electrode arrangement.

Feed lines to the heating element serve for supplying the heating element with electrical current. Typically, a heating element requires two feed lines in order to conduct current through the heating element. Typically, the feed lines are connected to electrical connectors which lead to an external current source or voltage source.

In this case, it is particularly preferred when the foil and the feed lines jointly form a contact tab laterally projecting from a face being occupied by the heating element. This facilitates a particularly simple manufacture, since the contact tab only has to be bent out of one plane. In this embodiment, the feed lines, which are part of the contact tab, can be connected to electrical connectors without the need of direct contact to the heating element.

Points at which electrical connectors are connected to feed lines, for example respective points on a contact tab, are preferably covered with an electrically insulating plastic material, particularly preferably with an epoxy resin. For this purpose, a plastic material, which is distributed under the trade name "Glob-Top", is suitable. Thereby, the covered portions are electrically insulated and protected against mechanical damages.

According to a second aspect, the invention relates to an electrosurgical gripping instrument with a stiff jaw, wherein the jaw carries an electrode arrangement according to one or several embodiments of the first aspect of the invention, wherein the heating element faces the jaw and the electrode faces the tissue. An electrosurgical gripping instrument typically has at least one handle part and two jaws the handle part facilitates to hold the electrosurgical gripping instrument in the hand. A jaw, on the other hand, is comprehended as the part of the electrosurgical gripping instrument which comes into contact with the tissue during gripping and which serves for exerting pressure to the tissue.

In an exemplary embodiment, a jaw is inflexibly connected to the handle part, while a second jaw is rotatably connected to the handle part. By rotating the additional jaw relative to the handle part and to the first jaw, the two jaws can jointly perform a plier-like gripping movement. Thereby, the further jaw is typically connected to the handle and to the first jaw through a link, for example through a swivel joint, a screwed joint or the like. In this case, the components of the electrosurgical gripping instrument, which are arranged on a side facing away from the handle part respective to the link, are typically designated as jaws.

Alternatively, the electrosurgical gripping instrument, however, can also have two handle parts, wherein each handle part, respectively, is inflexibly connected to a jaw, and wherein the two handle parts and their respective associated jaws are arranged relative to one another pivotable around a link. Through pinching the two handle parts together, in this case a plier-like gripping movement of the two jaws can be achieved.

By using an electrode arrangement according to the first aspect of the invention, the advantages of the electrode arrangement for the electrosurgical gripping instrument are realized. Thereby, preferably such respective electrode arrangement is provided on each of the two jaws, wherein the two electrode arrangements are facing towards one another. Alternatively, however, an electrode arrangement according to the first aspect of the invention can also be provided on only one jaw of the electrosurgical gripping instrument.

The jaw is typically configured inflexible to facilitate an exertion of the necessary pressure onto the tissue. For this purpose, the jaw typically consists fully or partially of stainless steel or another suitable material.

Additional features, advantages and embodiments of the invention are described with reference to the accompanying figures.

FIG. 2 illustrates a first embodiment of an electrode arrangement according to the first aspect of the invention;

FIG. 3b illustrates a modification of the embodiment of FIG. 3a;

Figure 1:
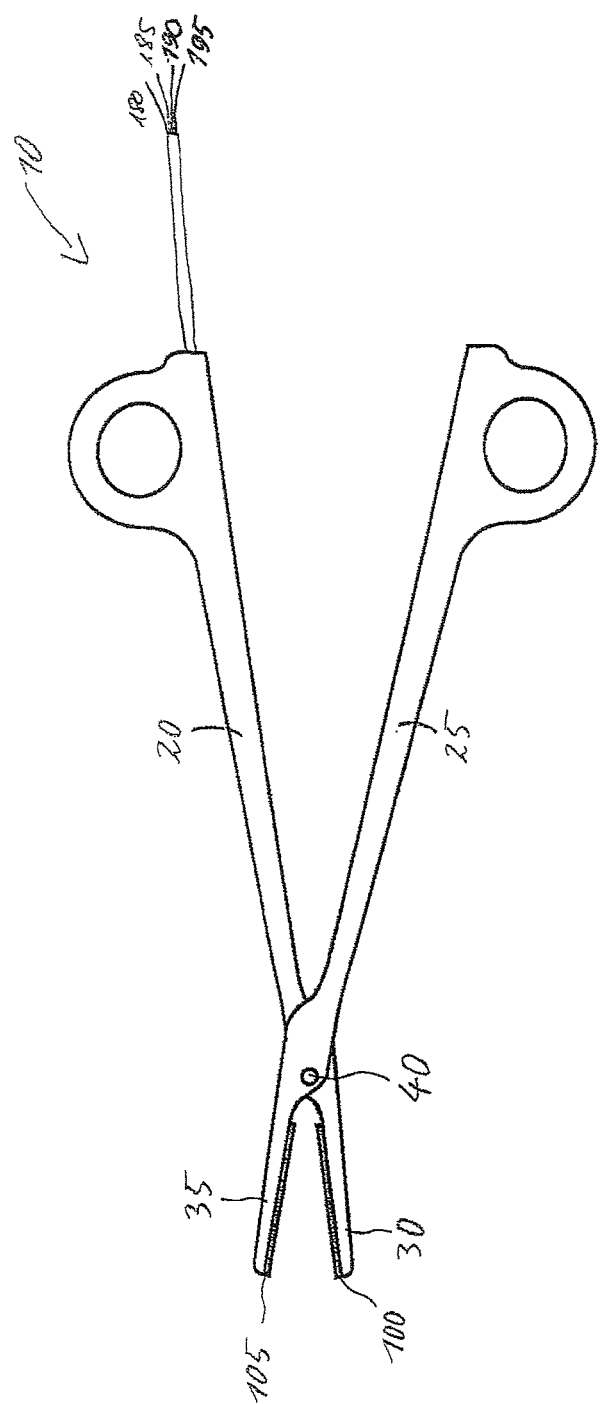
FIG. 1 illustrates an electrosurgical gripping instrument according to the second aspect of the invention.

FIG. 1 illustrates an electrosurgical gripping instrument 10 according to the second aspect of the invention with a first handle part 20 and a second handle part 25, a first jaw 30 and a second jaw 35. The first handle part 20 is inflexibly connected with the first jaw 30. Likewise, the first handle part 25 is inflexibly connected with the second jaw 35. At a respective transition between handle part and jaw, the first handle part 20 and the second handle part 25 are rotatably connected with one another by means of a swivel joint 40.

When the first handle part 20 is pushed towards the second handle part 25, the first jaw 30 and the second jaw 35 jointly perform a plier-like gripping movement.

The first jaw 30 carries a first electrode arrangement 100 which is facing towards the second jaw 35. Likewise, the second jaw 35 carries a second electrode arrangement 105 which is facing towards the first jaw 30. If the first jaw 30 and the second jaw 35 jointly perform a plier-like gripping movement, the first electrode arrangement 100 and the second electrode arrangement 105 move towards one another.

The electrosurgical gripping instrument 10 further includes connecting lines 180, 185, 190, 195 through which heating elements and electrodes of electrode arrangements can be energized. These are described infra.

Figure 3A:
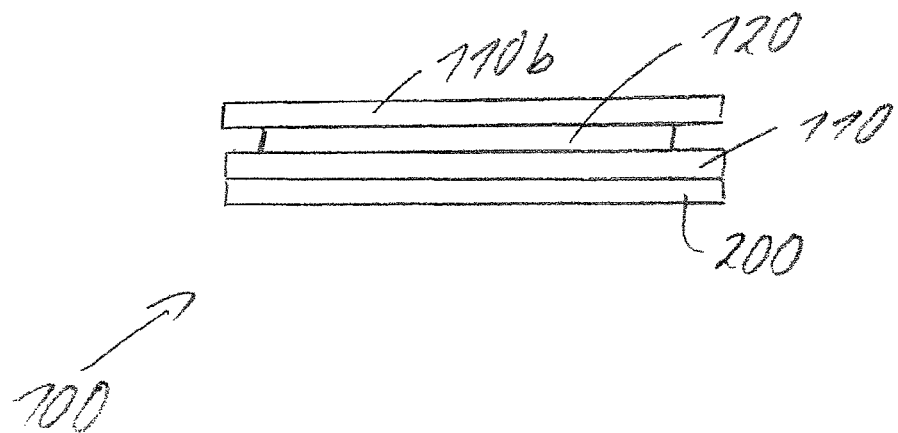
FIG. 3a illustrates a second embodiment of an electrode arrangement according to the first aspect of the invention.
Figure 3B:
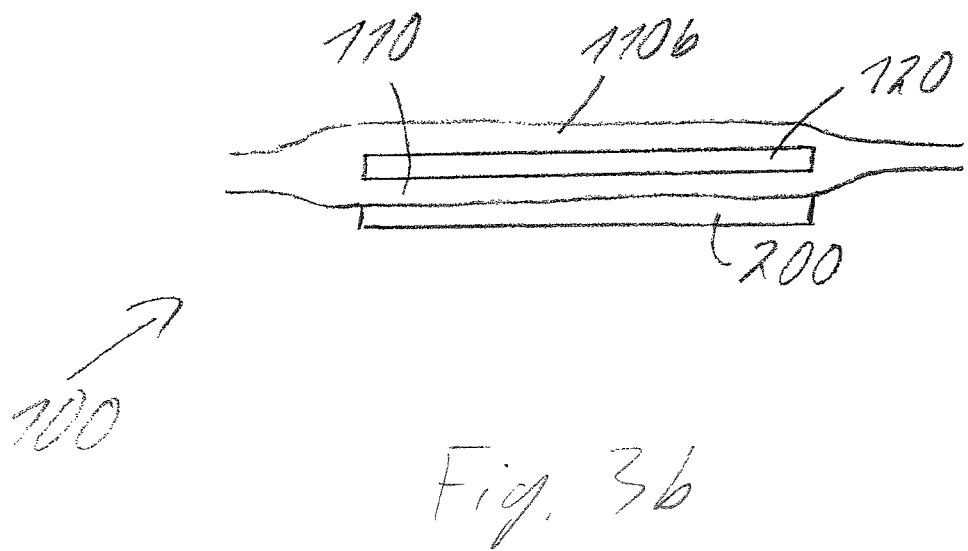
Figure 4:
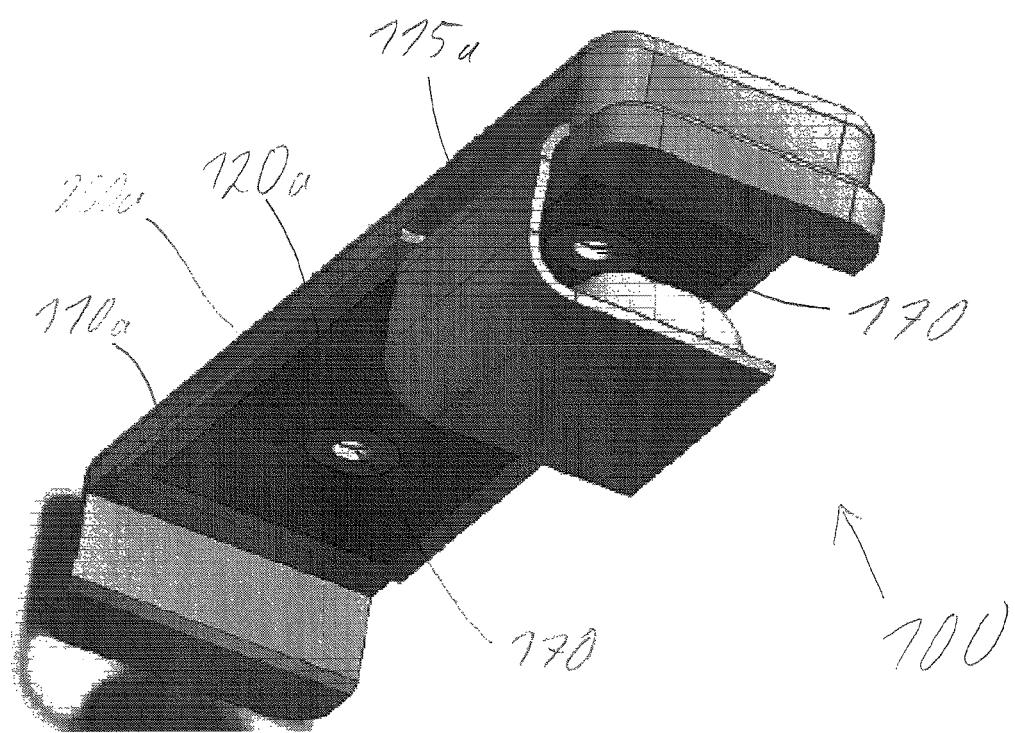
FIG. 4 illustrates a third embodiment according to an electrode arrangement according to the first aspect of the invention.

Suitable electrode arrangements 100, 105 are respectively described as electrode arrangements 100 in FIGS. 2-4.

FIG. 2 illustrates a first embodiment of an electrode arrangement 100 according to the first aspect of the invention. The electrode arrangement 100 includes an electrode 200 which is suitable for electrode-tissue contact. The electrode 200 is connectable with an HF energy source through a connecting line 190. An insulator 110 configured as a foil made from poly (4,4'-oxydiphenylenepyromellitimide) is applied onto the electrode 200.

The insulator requires more than 90% of the surface area of the electrode on one side. On the insulator 100, a heating element 120 in form of a heating wire is applied. This heating wire is partially configured in meandering shape in order to achieve an as far as possible even heating over a surface of the insulator 110 or the electrode 200, respectively.

The layers of the stack comprising electrode, insulator and heating element are interconnected in a good thermal conductive manner. This can be achieved for example through a suitable glue or also through laminating, printing or sputtering.

Furthermore, a first feed line 130 and a second feed line 135 for the heating element 120 are configured on the insulator 110. These are connected with a first contact pad 140 and a second contact pad 145. The heating element 120 can be electrically contacted by means of the contact pads 140, 145.

With its largest flat portion, the insulator 110 defines a plane. A small portion of the insulator 110 and the feed lines 130, 135 attached thereto, however, are bent together out of this plane to form a contact tab 115. Here it is configured in U-shaped form. Thereby, the contact pads 140, 145 can be contacted through connecting lines 180, 185 without occurring of any mechanical loading of the electrode arrangement 100. Further, on the contact pads 140, 145, are cover 160 made from epoxy resin is applied which protects the contact pads 140, 145 against mechanical or chemical damage.

FIG. 3a illustrates a second embodiment of an electrode arrangement 100 according to the first aspect of the invention in a sectional view. The view of FIG. 3a is not true to scale but only schematically. The insulator 110, the heating element 120 and the electrode 200, which are illustrated in FIG. 3a, have already been described with reference to FIG. 2.

The electrode arrangement in FIG. 3a illustrates a further insulator 110b, so that the heating element 120 is enveloped on both sides by an insulator 110, 110b. The insulator 110, 110b protrudes laterally beyond the heating element 120. In reality, the thicknesses of the insulators 110, 110b are only a few tenths or hundredths of a millimeter, e.g. 0.025 mm. The heating element has a thickness of 0.1 to 0.2 mm and the electrode has a thickness of approximately 1 mm.

A modification of the embodiment of FIG. 3a is illustrated in FIG. 3b. Herein, the heating element 120 is enclosed between the insulators 110, 110b, which together continue outside of the heating element 120 like a foil.

The insulator 110, 110b on both sides of the heating element 120 has the advantage that the heating element 120 is insulated from the material of the jaw 30, 35.

During a tissue fusion, the gripping element 10 with the electrode arrangements 100, 105 according to the invention is used as follows. The tissue layers to be fused are superimposedly engaged between the two jaws 30, 25. The two electrodes 200 of the electrode arrangement 100, 105 are connected through connecting lines 190, 195 to different poles of a bipolar output of a HF generator (not illustrated). The heating elements 120 are respectively connected through connecting lines 180, 185 to a further bipolar output of a HF generator. Alternatively, also the same bipolar output at the HF generator can be used, namely together with a switching device which can alternatively connect heating devices or electrodes.

Now, initially the supply of HF energy to the electrodes 200 is activated, for example through a handswitch or foot switch. As a result, a HF current flows between the electrodes 200 of the electrode arrangements 100, 105 through the tissue layers to be fused. The tissue is heated by the HF energy and tissue fusion starts.

Through the HF current, the tissue starts to dehydrate and the tissue resistance increases. Before it occurs that too little current flows to further heat and fuse the tissue, the heating elements 120 of the electrode arrangements 100, 105 are activated.

The HF electrodes 200 are deactivated, i.e. it is switched from one output to another output of the HF generator. By means of the heating elements 120, thermal energy is generated and transmitted through the electrodes 200 and passed to the tissue. Due to the supply of thermal energy, tissue fusion is sustained. When the tissue layers are sufficiently sealed, the heating elements are deactivated and the tissue fusion is completed. During tissue fusion, permanent pressure is exerted onto the tissue layers through the jaws 30, 35 which has an advantageous effect on the tissue fusion.

The heating elements 120 can, as an alternative to the alternating current of the HF generator, of course also be heated by direct current. However, alternating current is more advantageous.

FIG. 4 illustrates a third embodiment of an electrode arrangement 100 according to the first aspect of the invention.

This includes a flat electrode 200a, on which a flat insulator 110a is applied. On the insulator 110a, a heating element 120 is applied, which, in contrast to the heating element 120 of FIG. 2, is configured flat. Thereby, a particularly even heating of the electrode 200a is achieved.

Furthermore, the heating element 120a, the insulator 110a and the electrode 200a have three recesses 170 for temperature sensors, of which two of them are shown in FIG. 4. Thus, the recesses 170 are passages in the electrode arrangement. Temperature sensors, preferably optical temperature sensors, can be inserted into these recesses 170. In order not to influence the temperature measurement, the heating element 120a is configured radially offset from the circular recesses 170. Therewith, an insulation offset is provided.

Feed lines and connecting lines are not explicitly illustrated in FIG. 4. However, it is to be comprehended that the heating element 120a illustrated in FIG. 4 must to be supplied with electrical energy like the heating element 120 in FIG. 2. For this purpose, suitable feed lines are provided in a contact tab 115a, which is illustrated in FIG. 4.

Figure 5:
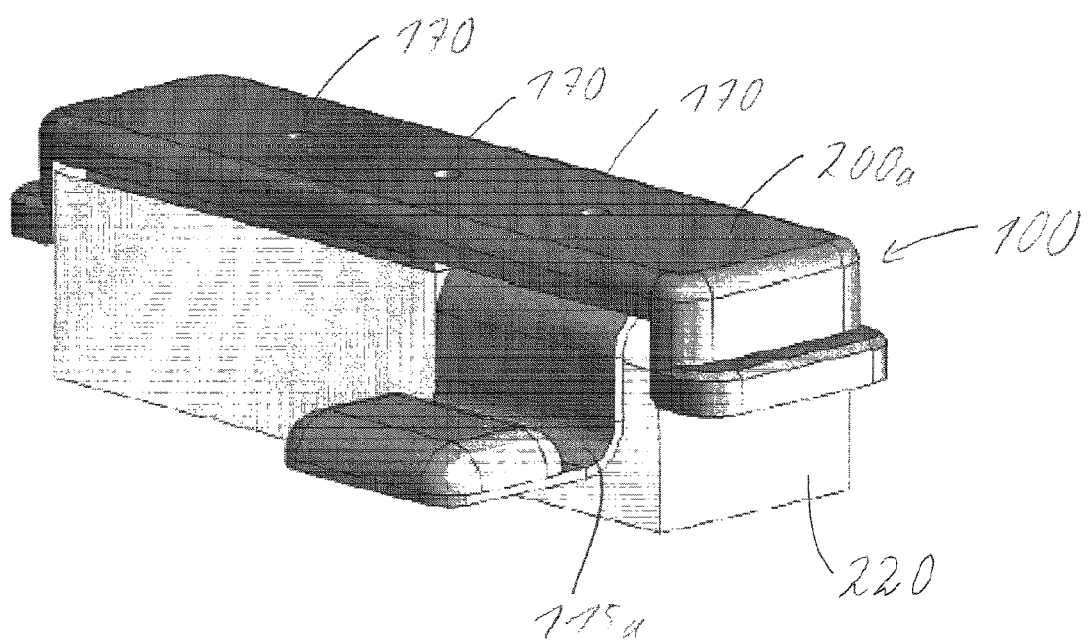
FIG. 5 illustrates the embodiment of FIG. 4 in an installed condition.

FIG. 5 illustrates the embodiment of FIG. 4 in installed condition. Therein, the electrode arrangement 100 is applied on a support block 220. The electrode 200a is clearly visible in this illustration, also the three recesses 170 for temperature sensors. The contact tab 115a, in comparison to FIG. 4, is bent differently; however, it has the same function.

The invention claimed is:

1. An electrode arrangement for an electrosurgical gripping instrument with an electrode, a heating element having feed lines for supplying the heating element with electrical current, and an electrically insulating thermally conductive insulator being arranged between the electrode and the heating element and electrically insulating them from one another, wherein
   the insulator is resilient;
   the insulator is a foil made from insulating, resilient plastic material, glass, ceramic or silicon on which the heating element and the feed lines for supplying the heating element with electrical current are applied; and
   the foil and the feed lines jointly form a contact tab which protrudes laterally from a surface which is covered by the heating element.

2. The electrode arrangement according to claim 1, wherein the insulator is configured flat.

3. The electrode arrangement according to claim 1, wherein the insulator is wholly or partially made of a flexible plastic material, glass, ceramic or silicon.

4. The electrode arrangement according to claim 3, wherein the plastic material is polyimide.

5. The electrode arrangement according to claim 3, wherein the plastic material is poly(4,4'-oxydiphenylene-pyromellitimide).

6. The electrode arrangement according to claim 1, wherein the heating element is at least two times as thick as the insulator.

7. The electrode arrangement according to claim 1 wherein the heating element covers more than 80% of a surface of the insulator, and wherein the insulator covers more than 80% of the surface of the electrode.

8. The electrode arrangement according to claim 1, wherein heating element has one or multiple recesses for temperature sensors.

9. The electrode arrangement according to claim 1, wherein the electrode, in comparison to the insulator, is inflexible.

10. The electrode arrangement according to claim 1, wherein the electrode is configured flat.

11. The electrode arrangement according to claim 1, wherein the heating element, the insulator and the electrode form a layer stack.

12. The electrode arrangement according to claim 1, wherein the heating element is four times as thick as the insulator.

13. An electrosurgical instrument including a stiff jaw, wherein the jaw supports an electrode arrangement with an electrode, a heating element having feed lines for supplying the heating element with electrical current, and an electrically insulating thermally conductive insulator being arranged between the electrode and the heating element and electrically insulating them from one another, wherein the insulator is resilient, the heating element is facing towards the jaw;

the insulator is a foil made from insulating, resilient plastic material, glass, ceramic or silicon on which the heating element and the feed lines for supplying the heating element with electrical current are applied; and the foil and the feed lines jointly form a contact tab which protrudes laterally from a surface which is covered by the heating element.

* * * * *